US006541207B1

(12) United States Patent
Vind et al.

(10) Patent No.: US 6,541,207 B1
(45) Date of Patent: *Apr. 1, 2003

(54) METHODS FOR GENERATING RECOMBINED POLYNUCLEOTIDES

(75) Inventors: Jesper Vind, Værløse (DK); Torben Vedel Borchert, Østerbro (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/687,301

(22) Filed: Oct. 13, 2000

Related U.S. Application Data

(63) Continuation of application No. 09/040,697, filed on Mar. 18, 1998, now Pat. No. 6,159,687.
(60) Provisional application No. 60/044,836, filed on Apr. 25, 1997, and provisional application No. 60/053,012, filed on Jun. 24, 1997.

(30) Foreign Application Priority Data

Mar. 18, 1997 (DK) ............................................. 0307/97
Apr. 17, 1997 (DK) ............................................. 0434/97
May 30, 1997 (DK) ............................................. 0625/97

(51) Int. Cl.$^7$ ........................ C12N 15/00; C12N 15/70; C12N 15/09; C12P 19/34; C07H 21/04
(52) U.S. Cl. ............................ 435/6; 435/4; 435/69.1; 435/91.1; 435/91.2; 435/455; 435/468; 435/471; 536/23.1
(58) Field of Search .......................... 435/6, 91.2, 91.5, 435/4, 69.1, 69.4–69.7, 91.1, 440, 455, 471, 476; 536/24.3, 24.31, 24.32, 23.1

(56) References Cited

U.S. PATENT DOCUMENTS

| 5,023,171 A | 6/1991 | Ho et al. |
| 5,093,257 A | 3/1992 | Gray |
| 5,629,179 A | 5/1997 | Mierendorf |

(List continued on next page.)

FOREIGN PATENT DOCUMENTS

| WO | WO/95/17413 | 6/1995 |
| WO | WO 95/22625 | 8/1995 |
| WO | WO/ 97/07205 | 2/1997 |

(List continued on next page.)

OTHER PUBLICATIONS

Marks et al., J. Mol. Biol., vol. 222, pp. 581–597 (1991).
Saiki et al., Reports, pp. 487–491 (Jan. 29, 1988).
Pääbo et al., The Journal of Biological Chemistry, vol. 265, No. 8, pp. 4718–4721 (Mar. 15, 1990).
Klug et al., Nucleic Acids Research, vol. 19, No. 10, p. 2793 (May 1991).
Krishnan et al., Nucleic Acids Research, vol. 19, No. 22, pp. 6177–6182.
Gerald F. Joyce, Scientific American, pp. 90–97 (Dec. 1992).
Clackson et al., Nature, vol. 352, 624–628 (Aug. 15, 1991).
Daugherty et al., Nucleic Acids Research, vol. 19, No. 9, pp. 2471–2476.
Yolov et al., Nucleic Acids Research, vol. 18, No. 13, pp. 3983–3986.
Kumud Majumder, Gene, vol. 110, pp. 89–94 (1992).
Jayaraman et al., Proc. Natl. Acad. Sci. USA, vol. 88, pp. 4084–4088 (May 1991).
Mark J. Zoller, Current Opinion in Biotechnology, vol. 3, pp. 348–354 (1992).
Horton et al., BioTechniques, vol. 8, No. 5, pp. 528–535 (1990).
Horton et al.; Methods in Enzymology, vol. 217, No. 17, pp. 270–279.
Ho et al., DNA and Protein Engineering Techniques, vol. 2, No. 2, pp. 50–55 (1990).
Weber et al., "Formation of Genes Coding For Hybrid Proteins By Recombination Between Related Cloned Genes in E. Coli", Institut For Molekularbiologie, I, Universitat Zurich, 8093 Zurich, Switzerland, pp. 5661–5669.
Pompon et al., "Protein Engineering by cDNA Recombination In Yeasts: Shuffling of Mammalian Cytochrome P–450 Functions", 1989 Elsevier Science Publishers B.V., pp. 15–24.
Stemmer et al, "DNA Shuffling By Random Fragmentation And Reassembly In Vitro Recombination For Molecular Evolution", Proc. Natl. Acad. Sci. USA, vol. 91, Oct. 1994, pp. 10747–10751.

*Primary Examiner*—Terry McKelvey
*Assistant Examiner*—Gerald G. Leffers, Jr.
(74) *Attorney, Agent, or Firm*—Elias J. Lambiris; Jason I. Garbell

(57) ABSTRACT

A method for in vitro construction of a library of recombined homologous polynucleotides from a number of different starting DNA templates and primers by induced template shifts during an polynucleotide synthesis is described, whereby A. extended primers are synthesized by
  a) denaturing the DNA templates
  b) annealing primers to the templates,
  c) extending the said primers by use of a polymerase,
  d) stop the synthesis, and
  e) separate the extended primers from the templates, B. a template shift is induced by
  a) isolating the extended primers from the templates and repeating steps A.b) to A.e) using the extended primers as both primers and templates, or
  b) repeating steps A.b) to A.e), C. this process is terminated after an appropriate number of cycles of process steps A. and B.a), A. and B.b), or combinations thereof.

Optionally the polynucleotides are amplified in a standard PCR reaction with specific primers to selectively amplify homologous polynucleotides of interest.

30 Claims, No Drawings

U.S. PATENT DOCUMENTS

| | | |
|---|---|---|
| 5,830,696 A | 11/1998 | Short |
| 5,939,250 A | 8/1999 | Short |
| 5,958,672 A | 9/1999 | Short |
| 6,001,574 A | 12/1999 | Short et al. |
| 6,004,788 A | 12/1999 | Short |
| 6,030,779 A | 2/2000 | Short |
| 6,159,687 A * | 12/2000 | Vind .......................... 435/6 |

FOREIGN PATENT DOCUMENTS

| | | |
|---|---|---|
| WO | WO 97/20078 | 6/1997 |
| WO | WO 97/35957 | 10/1997 |
| WO | WO 97/35966 | 10/1997 |
| WO | WO 98/01581 | 1/1998 |
| WO | WO 98/27230 | 6/1998 |
| WO | WO 98/31837 | 7/1998 |

* cited by examiner

METHODS FOR GENERATING RECOMBINED POLYNUCLEOTIDES

CROSS-REFERENCE TO RELATED APPLICATIONS

This application is a Rule 1.53(b) continuation application of U.S. patent application Ser. No. 09/040,697, filed Mar. 18, 1998, now U.S. Pat. No. 6,159,687 issued Dec. 12, 2000.

This application claims priority under 35 U.S.C. 119 of Danish applications 0307/97 filed Mar. 18, 1997, 0434/97 filed Apr. 17, 1997, and 0625/97 filed May 30, 1997, and U.S. Provisional applications Ser. Nos. 60/044,836, filed Apr. 25, 1997 and Ser. No. 60/153,012 filed Jun. 24, 1997, the contents of which are fully incorporated herein by reference.

FIELD OF THE INVENTION

The present invention relates to optimizing DNA sequences in order to (a) improve the properties of a protein of interest by artificial generation of genetic diversity of a gene encoding the protein of interest by the use of the so-called gene- or DNA shuffling technique to create a large library of "genes", expressing said library of genes in a suitable expression system and screening the expressed proteins in respect of specific characteristics to determine such proteins exhibiting desired properties or (b) improve the properties of regulatory elements such as promoters or terminators by generation of a library of these elements, transforming suitable hosts therewith in operable conjunction with a structural gene, expressing said structural gene and screening for desirable properties in the regulatory element.

BACKGROUND OF THE INVENTION

It is generally found that a protein performing a certain bioactivity exhibits a certain variation between genera and even between members of the same species differences may exist. This variation is of course even more outspoken at the genomic level.

This natural genetic diversity among genes coding for proteins having basically the same bioactivity has been generated in Nature over billions of years and reflects a natural optimization of the proteins coded for in respect of the environment of the organism in question.

In today's society the conditions of life are vastly removed from the natural environment and it has been found that the naturally occurring bioactive molecules are not optimized for the various uses to which they are put by mankind, especially when they are used for industrial purposes.

It has therefore been of interest to industry to identify such bioactive proteins that exhibit optimal properties in respect of the use to which it is intended.

This has for many years been done by screening of natural sources, or by use of mutagenesis. For instance, within the technical field of enzymes for use in e.g. detergents, the washing and/or dishwashing performance of e.g. naturally occurring proteases, lipases, amylases and cellulases have been improved significantly, by in vitro modifications of the enzymes.

In most cases these improvements have been obtained by site-directed mutagenesis resulting in substitution, deletion or insertion of specific amino acid residues which have been chosen either on the basis of their type or on the basis of their location in the secondary or tertiary structure of the mature enzyme (see for instance U.S. Pat. No. 4,518,584).

In this manner the preparation of novel polypeptide variants and mutants, such as novel modified enzymes with altered characteristics, e.g. specific activity, substrate specificity, thermal, pH and salt stability, pH-optimum, pI, $K_m$, $V_{max}$ etc., has successfully been performed to obtain polypeptides with improved properties.

For instance, within the technical field of enzymes the washing and/or dishwashing performance of e.g. proteases, lipases, amylases and cellulases have been improved significantly.

An alternative general approach for modifying proteins and enzymes has been based on random mutagenesis, for instance, as disclosed in U.S. Pat. No. 4,894,331 and WO 93/01285.

As it is a cumbersome and time consuming process to obtain polypeptide variants or mutants with improved functional properties a few alternative methods for rapid preparation of modified polypeptides have been suggested.

Weber et al., (1983), Nucleic Acids Research, vol. 11, 5661, describes a method for modifying genes by in vivo recombination between two homologous genes. A linear DNA sequence comprising a plasmid vector flanked by a DNA sequence encoding alpha-1 human interferon in the 5'-end and a DNA sequence encoding alpha-2 human interferon in the 3'-end is constructed and transfected into a rec A positive strain of E. coli. Recombinants were identified and isolated using a resistance marker.

Pompon et al., (1989), Gene 83, p. 15–24, describes a method for shuffling gene domains of mammalian cytochrome P-450 by in vivo recombination of partially homologous sequences in Saccharomyces cerevisiae by transforming Saccharomyces cerevisiae with a linearized plasmid with filled-in ends, and a DNA fragment being partially homologous to the ends of said plasmid.

In WO 97/07205 a method is described whereby polypeptide variants are prepared by shuffling different nucleotide sequences of homologous DNA sequences by in vivo recombination using plasmidic DNA as template.

U.S. Pat. No. 5,093,257 (Assignee: Genencor Int. Inc.) discloses a method for producing hybrid polypeptides by in vivo recombination. Hybrid DNA sequences are produced by forming a circular vector comprising a replication sequence, a first DNA sequence encoding the amino-terminal portion of the hybrid polypeptide, a second DNA sequence encoding the carboxy-terminal portion of said hybrid polypeptide. The circular vector is transformed into a rec positive microorganism in which the circular vector is amplified. This results in recombination of said circular vector mediated by the naturally occurring recombination mechanism of the rec positive microorganism, which include prokaryotes such as Bacillus and E. coli, and eukaryotes such as Saccharomyces cerevisiae.

One method for the shuffling of homologous DNA sequences has been described by Stemmer (Stemmer, (1994), Proc. Natl. Acad. Sci. USA, Vol. 91, 10747–10751; Stemmer, (1994), Nature, vol. 370, 389–391). The method concerns shuffling homologous DNA sequences by using in vitro PCR techniques. Positive recombinant genes containing shuffled DNA sequences are selected from a DNA library based on the improved function of the expressed proteins.

The above method is also described in WO 95/22625. WO 95/22625 relates to a method for shuffling of homologous DNA sequences. An important step in the method described in WO 95/22625 is to cleave the homologous template double-stranded polynucleotide into random fragments of a desired size followed by homologously reassembling of the fragments into full-length genes.

A disadvantage inherent to the method of WO 95/22625 is, however, that the diversity generated through that method is limited due to the use of homologous gene sequences (as defined in WO 95/22625).

Another disadvantage in the method of WO 95/22625 lies in the production of the random fragments by the cleavage of the template double-stranded polynucleotide.

A further reference of interest is WO 95/17413 describing a method of gene or DNA shuffling by recombination of specific DNA sequences—so-called design elements (DE)—either by recombination of synthesized double-stranded fragments or recombination of PCR generated sequences to produce so-called functional elements (FE) comprising at least two of the design elements. According to the method described in WO 95/17413 the recombination has to be performed among design elements that have DNA sequences with sufficient sequence homology to enable hybridization of the different sequences to be recombined.

WO 95/17413 therefore also entails the disadvantage that the diversity generated is relatively limited. Furthermore the method described is time consuming, expensive, and not suited for automatisation.

Despite the existence of the above methods there is still a need for better iterative in vitro recombination methods for preparing novel polypeptide variants. Such methods should also be capable of being performed in small volumes, and amenable to automatisation.

SUMMARY OF THE INVENTION

The present invention concerns briefly the utilization of template shift of a newly synthesized DNA strand during in vitro DNA synthesis in order to achieve DNA shuffling. By using this technique it is possible to obtain such results in a more expedient manner, and to some extent even a greater variation than in the above mentioned methods.

The method of the invention is also very well suited for adaption to automatisation.

In a preferred embodiment the technique is used in combination with an error-prone polymerase thereby introducing an even greater variation in the library created.

More specifically the present invention relates to a method for the construction of a library of recombined homologous polynucleotides from a number of different starting single or double stranded parental DNA templates and primers by induced template shifts during an in vitro polynucleotide synthesis using a polymerase, whereby A. extended primers or polynucleotides are synthesized by
  a) denaturing parental double stranded DNA templates to produce single stranded templates,
  b) annealing said primers to the single stranded DNA templates,
  c) extending said primers by initiating synthesis by use of said polymerase,
  d) cause arrest of the synthesis, and
  e) denaturing the double strand to separate the extended primers from the templates,
B. a template shift is induced by
  a) isolating the newly synthesized single stranded extended primers from the templates and repeating steps A.b) to A.e) using said extended primers produced in (A) as both primers and templates, or
  b) repeating steps A.b) to A.e),
C. the above process is terminated after an appropriate number of cycles of process steps A. and B.a), A. and B.b), or combinations thereof, and
D. optionally the produced polynucleotides are amplified in a standard PCR reaction with specific primers to selectively amplify homologous polynucleotides of interest.

In specific embodiments various modifications can be made in the process of the invention. For example it is advantageous to apply a defective polymerase either an error-prone polymerase to introduce mutations in comparison to the templates, or a polymerase that will discontinue the polynucleotide synthesis prematurely to effect the arrest of the reaction.

Further modifications will be described below.

In a further aspect the invention relates to a method of identifying polypeptides exhibiting improved properties in comparison to naturally occurring polypeptides of the same bioactivity, whereby a library of recombined homologous polynucleotides produced by the above process are cloned into an appropriate vector, said vector is then transformed into a suitable host system, to be expressed into the corresponding polypeptides and displayed, said polypeptides are then screened in a suitable assay, and positive results selected.

In a still further aspect the invention relates to a method for producing a polypeptide of interest as identified in the preceding process, whereby a vector comprising a polynucleotide encoding said polypeptide is transformed into a suitable host, said host is grown to express said polypeptide, and the polypeptide recovered and purified.

Finally, in further final aspects the invention relates to a recombined/shuffled protein, which is obtainable by any of the methods according to the invention, and which is a recombined/shuffled protein comprising the sequences disclosed herein (vide infra).

In those final aspects of the invention, the term "obtainable" denotes that said protein is preferable obtained by a method according to the invention. However a prior art known recombination/shuffling technique such as those described in WO 95/22625 or WO 95/17413 may be used too, either alone or in combination with a method according to the invention, in order to obtain said recombined protein.

Accordingly, further final aspect of the invention are;
  a recombined/shuffled protease obtainable by any of the methods according to the invention, and comprising a recombined sequence, which at least contain two different partial sequences from at least two different wild-type proteases;
  a recombined/shuffled lipase obtainable by any of the methods according to the invention, and comprising a recombined sequence, which at least contain two different partial wild-type sequences
  a recombined/shuffled Pseudomonas lipases obtainable by any of the methods according to the invention, and comprising a recombined sequence, which at least contain two different partial sequences from at least two of the different wild-type Pseudomonas lipases;
  a recombined/shuffled xylanase obtainable by any of the methods according to the invention, and comprising a recombined sequence, which at least contain two different partial sequences from at least two different wild-type xylanases;
  a recombined/shuffled cellulase obtainable by any of the methods according to the invention, and comprising a recombined sequence, which at least contain two different partial sequences from at least two different wild-type cellulases;

a recombined/shuffled amylase obtainable by any of the methods according to the invention, and comprising a recombined sequence, which at least contain two different partial sequences from at least two different wild-type amylases a recombined/shuffled laccase obtainable by any of the methods according to the invention, and comprising a recombined sequence, which at least contain two different partial sequences from at least two different wild-type laccases;

a recombined/shuffled phytase obtainable by any of the methods according to the invention, and comprising a recombined sequence, which at least contain two different partial sequences from at least two different wild-type phytases.

DEFINITIONS

Prior to discussing this invention in further detail, the following terms will first be defined.

"Shuffling": The term "shuffling" means recombination of nucleotide sequence fragment(s) between two or more homologous polynucleotides resulting in output polynucleotides (i.e. polynucleotides having been subjected to a shuffling cycle) having a number of nucleotide fragments exchanged, in comparison to the input polynucleotides (i.e. starting point homologous polynucleotides).

"Homology of DNA sequences or polynucleotides" In the present context the degree of DNA sequence homology is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wisconsin, USA 53711)(Needleman, S. B. and Wunsch, C. D., (1970), Journal of Molecular Biology, 48, 443–453).

"Homologous": The term "homologous" means that one singlestranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later (vide infra).

Using the computer program GAP (vide supra) with the following settings for DNA sequence comparison: GAP creation penalty of 5.0 and GAP extension penalty of 0.3, it is in the present context believed that two DNA sequences will be able to hybridize (using low stringency hybridization conditions as defined below) if they mutually exhibit a degree of identity preferably of at least 70%, more preferably at least 80%, and even more preferably at least 85%.

"heterologous": If two or more DNA sequences mutually exhibit a degree of identity which is less than above specified, they are in the present context said to be "heterologous".

"Hybridization:" Suitable experimental conditions for determining if two or more DNA sequences of interest do hybridize or not is herein defined as hybridization at low stringency as described in detail below.

Molecules to which the oligonucleotide probe hybridizes under these conditions are detected using a x-ray film or a phosphoimager.

"primer": The term "primer" used herein especially in connection with a PCR reaction is an oligonucleotide (especially a "PCR-primer") defined and constructed according to general standard specifications known in the art ("PCR A practical approach" IRL Press, (1991)).

"A primer directed to a sequence:"The term "a primer directed to a sequence" means that the primer (preferably to be used in a PCR reaction) is constructed to exhibit at least 80% degree of sequence identity to the sequence fragment of interest, more preferably at least 90% degree of sequence identity to the sequence fragment of interest, which said primer consequently is "directed to". The primer is designed to specifically anneal at the sequence fragment or region it is directed towards at a given temperature. Especially identity at the 3' end of the primer is essential.

"Flanking" The term "flanking" used herein in connection with DNA sequences comprised in a PCR-fragment means the outermost partial sequences of the PCR-fragment, both in the 5' and 3' ends of the PCR fragment.

"Polypeptide" Polymers of amino acids sometimes referred to as proteins. The sequence of amino acids determines the folded conformation that the polypeptide assumes, and this in turn determines biological properties and activity. Some polypeptides consist of a single polypeptide chain (monomeric), whereas other comprise several associated polypeptides (multimeric). All enzymes and antibodies are polypeptides.

"Enzyme" A protein capable of catalysing chemical reactions. Specific types of enzymes to be mentioned are such as amylases, proteases, carbohydrases, lipases, cellulases, oxidoreductases, esterases, etc. Of specific interest in relation to the present invention are enzymes used in detergents, such as proteases, lipases, cellulases, amylases, etc.

DETAILED DESCRIPTION OF THE INVENTION

The present invention relates in its first aspect to a method for the construction of a library of recombined homologous polynucleotides from a number of different starting single or double stranded parental DNA templates and primers by induced template shifts during an in vitro polynucleotide synthesis using a polymerase, whereby A. extended primers or polynucleotides are synthesized by
  a) denaturing a parental double stranded DNA template to produce single stranded templates,
  b) annealing said primers to the single stranded DNA templates,
  c) extending said primers by initiating synthesis by use of said polymerase,
  d) cause arrest of the synthesis, and
  e) denaturing the double strand to separate the extended primers from the templates, B. a template shift is induced by
  a) isolating the newly synthesized single stranded extended primers from the templates and repeating steps A.b) to A.e) using said extended primers produced in (A) as both primers and templates, or
  b) repeating steps A.b) to A.e), C. the above process is terminated after an appropriate number of cycles of process steps A. and B.a), A. and B.b), or combinations thereof, and D. optionally the produced polynucleotides are amplified in a standard PCR reaction with specific primers to selectively amplify homologous polynucleotides of interest.

According to the invention the polymerase may be a DNA or a RNA polymerase, specific polymerases to be mentioned are such as DNA polymerases like T4 polymerase, T7 polymerase, *E. coli* DNA polymerase I or the Klenow fragment of DNA polymerase I, or thermostable polymerases such as Taq, Amplitaq, Vent, Pwo.

One of the advantages of the invention is that it makes it possible to control the length of the extension of the primers in the reaction in a convenient manner.

This can be accomplished by various means such as choice of polymerase, the physical and chemical conditions during the action of the polymerase, e.g. pH, temperature, buffer, salt concentration, and addition of various chemicals.

It is known that various polymerases carry out the DNA synthesis at different rates (nucleotides incorporated pr. second). For example has the Klenow fragment of DNA polymerase I a limited extension rate compared to e.g. the Taq polymerase (Sambrook et al. 1989).

Polymerases also display differences in processivity, which is the average number of nucleotides incorporated before the polymerase dissociates from the template/extended primer; again the Klenow polymerase is an example of a polymerase with limited processivity.

The choice of polymerase is therefore an important means in controlling the average extension of the primers.

These conditions may also exert an influence on the fidelity of the polymerase (the rate by which point mutations are introduced; HIV reverse transcriptase is an example of a polymerase of low fidelity), a parameter useful in combining shuffling and mutagenesis.

In specific embodiments various modifications can be made in the process of the invention. For example it is advantageous to apply a defective polymerase either an error-prone polymerase to introduce mutations in comparison to the templates, or a polymerase that will discontinue the polynucleotide synthesis prematurely to effect the arrest of the reaction. Such a defective polymerases that could be mentioned is a Klenow polymerase having low processivity.

In another embodiment of the invention polymerase will be added after each cycle, if the polymerase used is not thermostable.

According to the invention the starting single or double stranded parental templates may be different in that they contain different point mutations in the same native polynucleotide (gene), or they can be homologous polynucleotides (genes) isolated from nature, which may be amplified by PCR, or they can be combinations thereof. The templates used in the process of the invention are hereby homologous showing an identity at the DNA level of e.g. more than 95%, 90%, 85%, 80%, 75%, 70%, 65%, 60%, 55%, or even more than 50% identity.

It may be advantageous to use pre-selected templates comprising mutations with improved properties of interest. The present recombination method of the invention will then recombine said improved mutations for subsequent screening for even further improvements in the properties of interest.

Said pre-selected templates with improved properties of interest may have been identified by standard procedures in the art comprising e.g. i) error-prone PCR of templates of interest followed by ii) screening/selection for templates with improved characteristic of interest. The mutagenesis frequency (low or high mutagenesis frequency) of the error-prone PCR step is preferably adjusted in relation to the subsequent screening capacity, i.e. if the screening capacity is limited the error-prone PCR frequency is preferably low. (i.e. one to two mutations in each template) (see WO 92/18645 for further details).

The arrest of the polymerase reaction in step A.d) may as indicated above be obtained in different ways, such as by raising the temperature, or adding specific reagents as described in WO 95/17413.

When raising the temperature for this purpose, it is preferred to use temperatures between 90° C. and 99° C.

When using chemical agents DMSO is a possibility. Appropriate procedures are mentioned in e.g. WO 95/17413.

The process of the invention uses annealing of the primers to the templates in step 1.b. In this context the annealing may be random or specific, meaning either anywhere on the polynucleotide or at a specific position depending on the nature of the primer.

Also, the primers to be used may be completely random primers (NNNNNNNNNNN)(SEQ ID NO: 1) (N meaning a mixture of the four bases (A, T, G, C) is used at a particular position in the primer during synthesis), semi-random primers, or specific primers.

If the extended primers produced are to be separated from the primers during the process it is convenient to use labeled templates in order to provide a simple means for separation, a preferred marker is biotin or digoxigenin.

According to the invention the number of cycles necessary will be less than 500, in most cases less than 200, and normally less than 100 cycles.

In an embodiment of the invention the above in vitro shuffling is combined with a subsequent in vivo shuffling by methods such as those described in WO 97/07205.

In its second aspect the invention relates to a method of identifying polypeptides exhibiting improved properties in comparison to naturally occurring polypeptides of the same bioactivity, whereby a library of recombined homologous polynucleotides produced by the above process are cloned into an appropriate vector, said vector is then transformed into a suitable host system, to be expressed into the corresponding polypeptides, said polypeptides are then screened in a suitable assay, and positive polypeptides selected.

In an embodiment it is contemplated that the polypeptides of interest encoded by the shuffled library are expressed as a suitable fusion protein (e.g. as a hybrid with gIII of bacteriphage M13/fd) in order to display said recombined polypeptide on the surface of phage or bacteria.

In a third aspect the invention relates to a method for producing a polypeptide of interest as identified in the preceding process, whereby a vector comprising a polynucleotide encoding said polypeptide is transformed into a suitable host, said host is grown to express said polypeptide, and the polypeptide recovered and purified.

The use of partial random (semi-random) or completely random primers (mixtures of bases in a selected number or all positions in the primer) as initiation point for the DNA synthesis provide certain novel possibilities for the combined use of shuffling and random mutagenesis.

It is often associated with difficulties to obtain an in vitro recombination of polynucleotides that display relatively limited homology. By the use of an embodiment of the invention even very diverse polynucleotides can be forced to recombine.

According to that embodiment at least two templates (or two pools of diverse templates) are applied. The novel synthesis of the one polynucleotide can then be based on only one strand (i.e. either the sense or the anti-sense strand), and the synthesis of the other polynucleotide is based the opposite strand.

This can be accomplished by isolating the complementary strands from the two templates, e.g. by having these strands labeled by biotin. Synthesis of DNA is initiated by annealing either specific, partly random or completely random primers to these templates and adding a suitable polymerase. This can be performed as either separate reactions for the different templates or in just one reaction. Synthesis should preferably be performed under conditions that favor production of relatively short new fragments. These fragments can subsequently be isolated from the templates based on the affinity label. A PCR reaction is carried out on these fragments and as the starting material originates from two different strands, the newly synthesized fragments must recombine in order to produce full length PCR products—a kind of forced recombination.

Also for this embodiment rapid PCR with short or no extension time can be applied advantageously in order to enhance recombination, especially if pools of templates are used for the two strands.

The length of the primer and the annealing temperature utilized in the process determines if random primers will anneal and the number of mismatches between the template and the primer that can be accommodated. By varying the primer length and the annealing temperature the method of the invention provides a means for achieving random mutagenesis within a certain nucleotide window representing the length of the primer. The method of the invention thereby provides substantial benefits compared to other random mutagenesis approaches, especially the high probability for several base substitutions close to each other in the primary sequence, e.g. the use of a completely random 20' mer (mixture of all four nucleotides in all 20 positions) will according to theory under given experimental conditions give a certain reasonably high probability for having several base substitutions close to each other.

Error prone PCR (=high mutagenesis frequency PCR) does not provide this possibility. Error prone PCR provides a very low probability for having more than one base substitution within one codon (coding for one amino acid in a translated polypeptide).

Obviously the substitution of only one base within a codon doesn't provide total random mutagenesis (at protein level) as only a limited set of amino acid substitutions can be obtained by one base substitution at DNA level (e.g. Methionine encoded by ATG-codon requires three base substitution to become the TGT or TGC-codon encoding Cysteine).

In one embodiment of the invention the process is therefore performed by using random or semi-random primers having a length of from 6 to 200 bp, preferably from 10 to 70 bp, and better from 15 to 40 bp.

One of the advantages in the method of the invention is the robustness. In some embodiments the constant presence of full length template provides a further advantage avoiding PCR contamination problems. Furthermore it is much less laborius, with less hands on, than other described methods, thereby providing excellent possibilities for automation.

PCR-primers:

The PCR primers are constructed according to the standard descriptions in the art. Normally they are 10–75 basepairs (bp) long. However, for the specific embodiment using random or semi-random primers the length may be substantially longer as indicated above.

PCR-reactions:

If not otherwise mentioned the PCR-reaction performed according to the invention are performed according to standard protocols known in the art.

The term "Isolation of PCR fragment" is intended to cover as broad as simply an aliquot containing the PCR fragment. However preferably the PCR fragment is isolated to an extend which remove surplus of primers, nucleotides templates etc.

In an embodiment of the invention the DNA fragment(s) is(are) prepared under conditions resulting in a low, medium or high-random mutagenesis frequency.

To obtain low mutagenesis frequency the DNA sequence (s) (comprising the DNA fragment(s)) may be prepared by a standard PCR amplification method (U.S. Pat. No. 4,683, 202 or Saiki et al., (1988), Science 239, 487–491).

A medium or high mutagenesis frequency may be obtained by performing the PCR amplification under conditions which increase the misincorporation of nucleotides, for instance as described by Deshler, (1992), GATA 9(4), 103–106; Leung et al., (1989), Technique, Vol. 1, No. 1, 11–15.

It is also contemplated according to the invention to combine the PCR amplification (i.e. according to this embodiment also DNA fragment mutation) with a mutagenesis step using a suitable physical or chemical mutagenizing-agent, e.g., one which induces transitions, transversions, inversions, scrambling, deletions, and/or insertions.

Expressing the Recombinant Protein from the Recombinant Shuffled Sequences

Expression of the recombinant protein encoded by the shuffled sequence in accordance with the second and third aspect of the present-invention may be performed by use of standard expression vectors and corresponding expression systems known in the art.

Screening and Selection

In the context of the present invention the term "positive polypeptide variants" means resulting polypeptide variants possessing functional properties which has been improved in comparison to the polypeptides producible from the corresponding input DNA sequences. Examples, of such improved properties can be as different as e.g. enhance or lowered biological activity, increased wash performance, thermostability, oxidation stability, substrate specificity, antibiotic resistance etc.

Consequently, the screening method to be used for identifying positive variants depend on which property of the polypeptide in question it is desired to change, and in what direction the change is desired.

A number of suitable screening or selection systems to screen or select for a desired biological activity are described in the art. Examples are:

Strauberg et al. (Biotechnology 13: 669–673 (1995) describes a screening system for subtilisin variants having Calcium-independent stability;

Bryan et al. (Proteins 1:326–334 (1986)) describes a screening assay for proteases having a enhanced thermal stability; and PCT-DK96/00322 describes a screening assay for lipases having improved wash performance in washing detergents.

An embodiment of the invention comprises screening or selection of recombinant protein(s), wherein the desired biological activity is performance in dish-wash or laundry detergents. Examples of suitable dish-wash or laundry detergents are disclosed in PCT-DK96/00322 and WO 95/30011.

If, for instance, the polypeptide in question is an enzyme and the desired improved functional property is the wash performance, the screening may conveniently be performed by use of a filter assay based on the following principle:

The recombination host cell is incubated on a suitable medium and under suitable conditions for the enzyme to be secreted, the medium being provided with a double filter comprising a first protein-binding filter and on top of that a second filter exhibiting a low protein binding capability. The recombination host cell is located on the second filter. Subsequent to the incubation, the first filter comprising the enzyme secreted from the recombination host cell is separated from the second filter comprising said cells. The first filter is subjected to screening for the desired enzymatic activity and the corresponding microbial colonies present on the second filter are identified.

The filter used for binding the enzymatic activity may be any protein binding filter e.g. nylon or nitrocellulose. The topfilter carrying the colonies of the expression organism may be any filter that has no or low affinity for binding proteins e.g. cellulose acetate or Durapore®. The filter may be pre-treated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent e.g. agarose, agar, gelatin, polyacrylamide, starch, filter paper, cloth; or any combination of immobilizing agents.

If the improved functional property of the polypeptide is not sufficiently good after one cycle of shuffling, the polypeptide may be subjected to another cycle.

In an embodiment of the invention wherein homologous polynucleotides representing a number of mutations of the same gene is used as templates at least one shuffling cycle is a back-crossing cycle with the initially used DNA fragment, which may be the wild-type DNA fragment. This eliminates non-essential mutations. Non-essential mutations may also be eliminated by using wild-type DNA fragments as the initially used input DNA material.

Also contemplated to be within the invention is polypeptides having biological activity such as insulin, ACTH, glucagon, somatostatin, somatotropin, thymosin, parathyroid hormone, pituary hormones, somatomedin, erythropoietin, luteinizing hormone, chorionic gonadotropin, hypothalamic releasing factors, antidiuretic hormones, thyroid stimulating hormone, relaxin, interferon, thrombopoeitin (TPO) and prolactin.

A requirement to the starting parental DNA sequences, encoding the polypeptide(s), to be shuffled, is that they are at least 50%, 60%, 70%, 80%, 90%, or 95% homologous. DNA sequences being less homologous will have less inclination to interact and recombine.

It is also contemplated according to the invention to shuffle parental polynucleotides that are homologous as indicated above originating from wild type organisms of different genera.

Further, the starting parental templates to be shuffled may preferably have a length of from about 50 bp to 20 kb, preferably about 100 bp to 10 kb, more preferred about 200 bp to 7 kb, especially about 400 bp to 2 kb.

The starting parental DNA sequences may be any DNA sequences including wild-type DNA sequences, DNA sequences encoding variants or mutants, or modifications thereof, such as extended or elongated DNA sequences, and may also be the outcome of DNA sequences having been subjected to one or more cycles of shuffling (i.e. output DNA sequences) according to the method of the invention or any other method (e.g. any of the methods described in the prior art section).

When using the method of the invention the resulting recombined homologous polynucleotides (i.e. shuffled DNA sequences), have had a number of nucleotide fragments exchanged. This results in replacement of at least one amino acid within the polypeptide variant, if comparing it with the parent polypeptide. It is to be understood that also silent exchanges are contemplated (i.e. nucleotide exchange which does not result in changes in the amino acid sequence).

MATERIALS AND METHODS

Specific Method Used in the Examples:

A) DNA encoding different enzyme variants of the same gene or different enzymes having the same type of activity encoded by homologous genes are mixed. The DNA is provided as either PCR fragments, plasmid, phage or genomic DNA.

B) The resulting pool of DNA is mixed with DNA Polymerase, dNTP, a suitable buffer and primers (being either random oligomers (length of 6–30 nucleotides) or specific oligomers (length of 6–50 nucleotides) or a combination of both types).

C) The PCR mixture is put into a PCR thermocycler (either cold or hot) in a suitable tube.

c1) The thermocycler is heated to a temperature of 90–100° C. for a period of time(typically 1–10 min) in order to denature the DNA templates.

c2) Thereafter the following procedure (cycle) is followed (repeated): The template is denatured (typically 90–100° C. for 0–5 minutes). Then the temperature is lowered (typically to a value between 10° C. and 90° C. for 0–5 minutes) to allow annealing of the primer to the single stranded template. Now the temperature is raised again to denaturation temperature (90–100° C.) allowing small extension of the primer to be synthesized by the DNA polymerase during ramping. Alternatively a short extension period (typically 0–30 seconds at 70–75° C.) can be introduced to allow larger extensions of the primers to be generated. When the temperature reaches a value where denaturation takes place, the extended primers and templates are again separated. This procedure can be repeated (typically between 1 to 99 cycles).

D) Having performed the desired number of cycles the generated small DNA polymers can be purified from the oligomers used as primers. One way is to isolate and clone a specific amplified band containing the gene coding for the polypeptide of interest into a suitable vector. This can be done either on agarose gel (typically isolating fragments between 50 to 1000 base pairs), by beads (using an affinity label on either templates or primers) or through columns.

E) Then the purified (or the not purified) DNA polymers can be assembled in a standard PCR reaction (for instance 94° C., 5 minutes, (94° C., 30 sec; 55° C., 30 sec; 72° C., 2 min)*25, 72° C. 5 minutes, 4° C.).

Specific primers or DNA polymers generated by specific primers can be added in order to generate a specific DNA polymer containing the gene of interest. This As mentioned in point D, this DNA polymer can be purified and cloned into a vector of interest.

EXAMPLES

Example 1

Method 1

The strong advantage of the method exemplified here is the robustness and lack of PCR contamination problems, due to the constant presence of parental template. Furthermore this method is less labor demanding than methods described in the prior art, thereby providing excellent possibilities for automation.

Nine different plasmids containing DNA sequences encoding 9 different variants of the *H. lanuginosa* lipase gene, were mixed in equimolar amounts. The variant genes contained from two to seven mutations scattered throughout the gene.

The DNA sequence of the *H. lanuginosa* lipase gene and the amino acid sequence of the lipase are disclosed in EP 0 305 216

The variants are indicated according to standard terminology as described in e.g. EP 0 396 608, and WO 97/07202.

The following 9 variant genes were shuffled:
1'. N94+D96L+E99K
2'. SPPRRP (SEQ ID NO: 2)+N94K+D96L+T231R+N233R+D234R+Q249R
3'. SPPRRP (SEQ ID NO: 2)+A19C+C36A+N94K+D96L+Q249R
4'. STPRRP (SEQ ID NO: 3)+N94R
5'. SCIRR (SEQ ID NO: 4)+N94K+D96L+E239C+Q249R
6'. D137G+D167G+E210V
7'. D96L+E99K+V187A
8'. SPPRRP (SEQ ID NO: 2)+D57G+N94K+D96L+Q249R
9'. N94R+F95L The following components where mixed in a microtube:
2 $\mu$l plasmid mixture (0.15 $\mu$g/$\mu$l), specific primers flanking the gene (1 pmol/$\mu$l), 2 $\mu$l 2.5 mM dNTP, 2.5 mM MgCl$_2$, 2 $\mu$l 10*taq buffer (Perkin Elmer), 0.5 $\mu$l taq enzyme in a total volume of 20 $\mu$l.

The tube was set in a Perkin Elmer 2400 thermocycler. The following PCR-program was run:(94° C., 5 minutes) 1 cycle: (94° C. , 30 seconds, 70° C., 0 seconds) 99 cycles(72° C., 2 minutes, 4° C. indefinite) 1 cycle The PCR-reaction was run on a 1.5% agarose gel. A DNA-band of the specific expected size was cut out of the agarose gel and purified using JETsorb (from GENOMED Inc.). The purified PCR-product was cloned into a TA-vector (from Invitrogen (the original TA cloning kit). The ligated product was transformed into a standard *Escherichia coli* strain (DH5a).

20 transformants where fully sequenced across the gene of interest.

Result:
The following 20 variants were found:
1. D137G+D167G+E210V+Y213C
2. SPPRRP (SEQ ID NO: 2)+D57G+N94K+D96L+Q249R
3. N94R+F95L
4. SPPRRP (SEQ ID NO: 2)+D137G+D167G+E210V
5. N94K+D96L+E99K+V187A+T267I
6. D137G+D167G+E210V
7. N94K+D96L+E99K+V187A
8. D57G+N94R+F95L+Q249R
9. N94K+D96L+E99K+E210V
10. SPPRRP (SEQ ID NO: 2)+A19C+C36A+N94K+D96L
11. N94R+F95L
12. D137G+D167G+E210V
13. N94K+D96L+Q249R
14. SPPRRP (SEQ ID NO: 2)+Q15P+A19C+C36A+N94K+D96L
15. SPPRRP (SEQ ID NO: 2)+N94K+D96L+T231R+N233R+D234R+Q249R
16. D137G+D167G+E210V
17. SCIRR (SEQ ID NO: 4)+N94K+D96L+Q249R
18. N94K+D96L+E99K
19. N94R+F95L
20. SPPRRP (SEQ ID NO: 2)+N94R+F95L+F113S+Q249R Nearly all mutations where represented (19 of 20) indicating little bias for specific templates.

| Statistics: | |
|---|---|
| Not shuffled | 10 |
| Shuffled between at least 2 templates | 8 |
| Shuffled between at least 3 templates | 2 |

The shuffled sequences can then be subcloned from the *E. coli* TA vector into the yeast vector pJSO26 as a BamHI-XbaI fragment (see WO 97/07205), and e.g. screened for new shuffled sequences with improved performance in detergents (see WO 97/07205).

Example 2

Method 2:
PCR products of 10 different lipase variant genes were generated as above and pooled in equimolar amounts.

The following 10 mutant genes were shuffled.
1'. D137G+D167G+E210V
2'. D96L+E99K+V187A
3'. N94K+D96L+E99K
4'. SPPRRP (SEQ ID NO: 2)+D57G+N94K+D96L+Q249R
5'. D111N+F211A+G225P
6'. SPPRRP (SEQ ID NO: 2)+N94K+D96L+T231R+N233R+D234R+Q249R
7'. SPPRRP (SEQ ID NO: 2)+A19C+C36A+N94K+D96L+Q249R
8'. STPRRP (SEQ ID NO: 3)+N94R
9'. N94R+F95L
10'. SCIRR (SEQ ID NO: 4)+N94K+D96L+E239C+Q249R The following mixture was generated in a suitable tube:
1 $\mu$l PCR mixture (0.1 $\mu$g), decamer random primer (300 pmol), 2 $\mu$l 10*Klenow buffer (Promega), 0.25 mM dNTP, 2.5 mM MgCl$_2$ in a total volume of 20 $\mu$l.

The mixture was set in a PE2400 thermocycler where the following program was run: 96° C., 5 minutes, 25° C. 5 minutes, 0.5 ml Klenow enzyme was added, 25° C. 60 minutes, 35° C. 90 minutes.

This procedure generated a high number of small DNA polymers originating from all parts of the gene.

10 $\mu$l was taken out for test on agarose gel.

10 $\mu$l PCR mixture (0.25 mM DNTP, 1 $\mu$l 10*Taq buffer (Perkin Elmer), 2.5 mM MgCl$_2$, 0.5 $\mu$l Taq enzyme) was added to the 10 $\mu$l in the tube in the thermocycler. Then the following standard PCR-program was run: (94° C., 5 minutes) 1 cycle, (94° C. 30 seconds, 45° C., 30 seconds, 72° C. 30 seconds) 25 cycles, 72° C. 7 minutes, 4° C. indefinite.

The PCR products were run on a 1.5% agarose gel. A clear unbiased smear was seen. DNA between 400 and 800 bp was isolated from the gel.

Half of the purified PCR product was mixed in a tube with two specific primers (40 pmol) flanking the gene of interest, 0.25 mM DNTP, 2 $\mu$l 10*Taq buffer, 2.5 mM MgCl$_2$. Then the following standard PCR-program was run: (94° C. , 5 minutes) 1 cycle, (94° C. 30 seconds, 50° C., 30 seconds, 72° C. 30 seconds) 25 cycles, 72° C. 7 minutes, 4° C. indefinite.

The PCR product was run on a 1.5% agarose gel. A specific though weak band of the expected size was isolated. Additional PCR was run using specific primers (as mentioned above) in order to amplify the PCR-product before cloning.

The PCR-product and the desired vector were cut with the appropriate restriction enzymes (BamHI/XhoI). The vector and the PCR product were run on a 1.5% agarose gel, and purified from the gel.

The cut PCR-product and the cut vector were mixed in a ligase buffer with T4 DNA ligase (Promega). After overnight ligation at 16° C. the mixture was transformed into *E. coli* strain DH5a.

19 clones were fully sequenced across the gene.

Result:

The following 19 variants were found:

1. STPRRP (SEQ ID NO: 3)+N94R+N233R+D234R+Q249R
2. SPPRRP (SEQ ID NO: 2)+N233R+D234R+Q249R
3. D96L+D167G+Q249R
4. N94R
5. D167G
6. SPPRRP (SEQ ID NO: 2)+A19C+A28T+N94K+D96L+D111N+E239C
7. SPPRRP (SEQ ID NO: 2)+A19C+C36A+N94K+D96L+Q249R
8. N94K+D96L
9. N25T+D57G+N94R+E99K+D167G+T231R+N233R+D234R+Q249R
10. N94R+Q249R
11. D167G
12. D167G
13. T32I+N94R+F95L+D167G+Q249R
14. E87K+N94K+D96L
15. N94R+F95L+Q249R
16. N94K+D96L+D111N
17. STPRRP (SEQ ID NO: 3)+S17T
18. N94K+D96L+V187A
19. SPPRRP (SEQ ID NO: 2)+D57G+N94K+D96L+D111N+L151S

All template variants were represented indicating little bias for specific templates.

There were no apparent hot spots with regard to mutation exchange and it seems to be evenly distributed along the gene

| Statistics: | |
|---|---|
| Not shuffled | 1 |
| Shuffled between at least 2 templates | 10 |
| Shuffled between at least 3 templates | 6 |
| Shuffled between at least 4 templates | 1 |
| Shuffled between at least 5 templates | 0 |
| Shuffled between at least 6 templates | 1 |

The shuffled sequences can then be subcloned from the *E.coli* TA vector into the yeast vector pJSO26 as a BamHI-XbaI fragment (see WO 97/07205) and e.g. screened for new shuffled sequences with improved performance in detergents (see WO 97/07205).

Example 3

Amylase Variant Shuffling:

In Example 1, it was shown how a number of multiple variants of *H. lanuginosa* lipase were shuffled. In a similar manner, variants of Bacillus α-amylases can be shuffled.

Earlier patent applications have identified variants of various α-amylases from Bacillus species improved for particular properties, e.g. thermostability, stability under Calcium-depleted conditions, improved wash-performance etc. (see WO95/10603, WO96/23874, WO96/23873, and PCT/DK97/00197).

Variants of *B. licheniformis* α-amylase amyL can be shuffled as follows. The variants are all located in the *B. subtilis* expression vector pDN1528 described in WO95/10603.

The experiment is carried out under the exact same conditions as Example 1 except that the flanking 27mer primers used to initiate DNA synthesis were different.

The PCR amplified band of approximately 1500 bp is purified from an agarose gel and cloned as described in Example 1. Alternatively restriction sites located within the amyL gene can be utilized to clone the library of shuffled genes into either Bacillus plasmid pDN1528 or an *E. coli* vector containing the wild type amyL gene, e.g. pJeEN1 described in WO96/23874

Example 4

Shuffling of two genes encoding homologous α-amylases: amyL and the amylase identified by SEQ.ID no2 (amino acid) and SEQ.ID no. 5 (DNA) described in WO96/23873.

The forward strand (identical to the mRNA) of amyL can be amplified in a PCR using standard conditions.

The forward strand is separated from the reverse strand based on its affinity to streptavidin coated magnetic beads and denaturation of the two strands with NaOH. Similarly the reverse strand (complementary to mRNA) of the amylase encoded by SEQ.ID no5 (WO96/23873) can be amplified and isolated Two primer strands are used as templates in a PCR: (94° C. 5 minutes)+99 cycles of (94° C., 30 seconds; 60° C., 0 seconds)+(72° C., 5 minutes) using random primers of various lengths, Taq polymerase and standard buffer conditions as described in Example 1.

The resulting approximately 1500 bp product is cloned either as TA cloning as described in Example one (for verification of the sequence of the resulting clone) or into Bacillus vector, pTVB110 utilizing SfiI and PstI restriction sites.

The original template can be removed from the PCR at any step (e.g. after 5, 10 or 20 cycles) based on the biotin tag).

We claim:

1. A method of shuffling polynucleotides, comprising:
   (a) shuffling first strands of a first population of polynucleotides with second strands of a second population of polynucleotides, without shuffling second strands of the first population and first strands of the second population; and
   (b) synthesizing strands complementary to the shuffled first strands to form shuffled duplex polynucleotides.

2. The method of claim 1, wherein the first strands are isolated from the second strands by labeling the first strands with biotin.

3. The method of claim 1, wherein the first strands are a pool of polynucleotides comprising diverse forms of a polynucleotide.

4. The method of claim 3, wherein the diverse forms of the polynucleotide are from naturally occurring organisms of different species.

5. The method of claim 3, wherein the pool of polynucleotides exhibit more than 50% sequence identity.

6. The method of claim 3, wherein the pool of polynucleotides exhibit more than 70% sequence identity.

7. The method of claim 3, wherein the pool of polynucleotides exhibit more than 90% sequence identity.

8. The method of claim 3, wherein the pool of polynucleotides exhibit more than 95% sequence identity.

9. The method of claim 1, wherein the first strands are contacted with at least one completely random primer.

10. The method of claim 1, wherein the first strands are contacted with at least one partly random primer or at least a pair of partly random primers.

11. A method of identifying polypeptides exhibiting a desired property, comprising the method of claim 1, further comprising expressing and screening polypeptides encoded by the shuffled duplex polynucleotides for a desired property.

12. The method of claim 11, wherein the property is an enzymatic activity.

13. The method of claim 11, wherein at least one extension cycle is conducted under conditions of incomplete elongation.

14. The method of claim 11, wherein the first population of polynucleotides encode variant forms of an enzyme.

15. The method of claim 14, wherein the enzyme is selected from the group consisting of carbonyl hydrolase, carbohydrase, an esterase, a protease, a lipase, an amylase, a cellulase, an oxidase, and an oxido reductase.

16. The method of claim 11, wherein the frist population of polynucleotides comprises at least two variant polynucleotides and wherein the variant polynucleotides encode a polypeptide selected from the group consisting of insulin, ACTH, glucagon, somatostatin, somatotropin, thymosin, parathyroid hormone, pituary hormones, somatomedin, erythropoietin, luteinizing hormone, chorionic gonadotropin, hypothalamic releasing factors, antidiuretic hormones, thyroid stimulating hormone, relaxin, interferon, thrombopoeitin (TPO) and prolactin.

17. A method of shuffling polynucleotides, comprising:
   (a) isolating first strands of a first population of polynucleotides from second strands of the first population of polynucleotides and isolating first strands of a second population of polynucleotides from second strands of the second population of polynucleotides;
   (b) shuffling first strands of the first population of polynucleotides with second strands of the second population of polynucleotides, without shuffling second strands of the first population of polynucleotides and first strands of the second population of polynucleotides;
   (c) synthesizing strands complementary to the shuffled first strands to form shuffled duplex polynucleotides.

18. The method of claim 17, wherein the first strands are isolated from the second strands by labeling the first strands with biotin.

19. The method of claim 17, wherein the first strands are a pool of polynucleotides comprising diverse forms of a polynucleotide.

20. The method of claim 19, wherein the diverse forms of the polynucleotide are from naturally occurring organisms of different species.

21. The method of claim 17, wherein the pool of polynucleotides exhibit more than 50% sequence identity.

22. The method of claim 17, wherein the pool of polynucleotides exhibit more than 70% sequence identity.

23. The method of claim 17, wherein the pool of polynucleotides exhibit more than 90% sequence identity.

24. The method of claim 19, wherein the pool of polynucleotides exhibit more than 95% sequence identity.

25. A method of identifying polypeptides exhibiting a desired property, comprising the method of claim 4, further comprising expressing and screening polypeptides encoded by the shuffled duplex polynucleotides for a desired property.

26. The method of claim 25, wherein the property is an enzymatic activity.

27. The method of claim 25, wherein at least one extension cycle is conducted under conditions of incomplete elongation.

28. The method of claim 25, wherein the first population of polynucleotides encode variant forms of an enzyme.

29. The method of claim 28, wherein the enzyme is selected from the group consisting of carbonyl hydrolase, carbohydrase, an esterase, a protease, a lipase, an amylase, a cellulase, an oxidase, and an oxido reductase.

30. The method of claim 25, wherein the first population of polynucleotides comprises at least two variant polynucleotides and wherein the variant polynucleotides encode a polypeptide selected from the group consisting of insulin, ACTH, glucagon, somatostatin, somatotropin, thymosin, parathyroid hormone, pituary hormones, somatomedin, erythropoietin, luteinizing hormone, chorionic gonadotropin, hypothalamic releasing factors, antidiuretic hormones, thyroid stimulating hormone, relaxin, interferon, thrombopoeitin (TPO) and prolactin.

* * * * *

SEQUENCE LISTING

<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n denotes a, g, c, or t
<220> FEATURE:
<221> NAME/KEY: misc_feature
<222> LOCATION: (2)..(2)
<223> OTHER INFORMATION: n denotes a, g, c, or t
<220> FEATURE:
<221> NAME/KEY: misc_feature
<222> LOCATION: (3)..(3)
<223> OTHER INFORMATION: n denotes a, g, c, or t
<220> FEATURE:
<221> NAME/KEY: misc_feature
<222> LOCATION: (4)..(4)
<223> OTHER INFORMATION: n denotes a, g, c, or t
<220> FEATURE:
<221> NAME/KEY: misc_feature
<222> LOCATION: (5)..(5)
<223> OTHER INFORMATION: n denotes a, g, c, or t
<220> FEATURE:
<221> NAME/KEY: misc_feature
<222> LOCATION: (6)..(6)
<223> OTHER INFORMATION: n denotes a, g, c, or t
<220> FEATURE:
<221> NAME/KEY: misc_feature
<222> LOCATION: (7)..(7)
<223> OTHER INFORMATION: n denotes a, g, c, or t
<220> FEATURE:
<221> NAME/KEY: misc_feature
<222> LOCATION: (8)..(8)
<223> OTHER INFORMATION: n denotes a, g, c, or t
<220> FEATURE:
<221> NAME/KEY: misc_feature
<222> LOCATION: (9)..(9)
<223> OTHER INFORMATION: n denotes a, g, c, or t
<220> FEATURE:
<221> NAME/KEY: misc_feature
<222> LOCATION: (10)..(10)
<223> OTHER INFORMATION: n denotes a, g, c, or t
<220> FEATURE:
<221> NAME/KEY: misc_feature
<222> LOCATION: (11)..(11)
<223> OTHER INFORMATION: n denotes a, g, c, or t

<400> SEQUENCE: 1
nnnnnnnnnn n                                                          11

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Ser Pro Pro Arg Arg Pro
1               5

<210> SEQ ID NO 3
<211> LENGTH: 6
<212> TYPE: PRT
<213> ORGANISM: Artificial Sequence
<220> FEATURE:

```
-continued

<223> OTHER INFORMATION: Synthetic

<400> SEQUENCE: 3

Ser Thr Pro Arg Arg Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser Cys Ile Arg Arg
1               5
```